US006893685B2

(12) United States Patent
Qiu et al.

(10) Patent No.: US 6,893,685 B2
(45) Date of Patent: May 17, 2005

(54) PROCESS FOR SURFACE MODIFYING SUBSTRATES AND MODIFIED SUBSTRATES RESULTING THEREFROM

(75) Inventors: Yongxing Qiu, Duluth, GA (US); Lynn Cook Winterton, Alpharetta, GA (US); John Martin Lally, Lilburn, GA (US); Paul Pasic, Melbourne (AU); Hans Griesser, The Patch (AU); Peter Kambouris, Carindale (AU); Peter Chabrecek, Riehen (CH)

(73) Assignee: Novartis AG, Basel (CH)

( * ) Notice: Subject to any disclaimer, the term of this patent is extended or adjusted under 35 U.S.C. 154(b) by 528 days.

(21) Appl. No.: 09/939,145

(22) Filed: Aug. 24, 2001

(65) Prior Publication Data

US 2002/0086160 A1 Jul. 4, 2002

Related U.S. Application Data

(60) Provisional application No. 60/228,022, filed on Aug. 24, 2000.

(51) Int. Cl.$^7$ .................................................. B05D 1/36
(52) U.S. Cl. .............................. 427/407.1; 427/412.1; 427/2.12; 427/2.13; 427/2.24; 428/447; 428/451; 428/515; 428/520; 351/159; 351/160 R
(58) Field of Search ............................ 427/2.12, 2.13, 427/2.24, 407.1, 412.1; 428/447, 451, 515, 520; 351/159, 160 R

(56) References Cited

U.S. PATENT DOCUMENTS

| | | | |
|---|---|---|---|
| 4,168,112 A | 9/1979 | Ellis et al. ................... | 351/160 |
| 4,321,261 A | 3/1982 | Ellis et al. ................... | 424/180 |
| 4,941,997 A | 7/1990 | Decher et al. ............... | 252/586 |
| 4,973,429 A | 11/1990 | Decher et al. ............... | 252/587 |
| 5,068,318 A | 11/1991 | Decher et al. ............... | 534/573 |
| 5,518,767 A | 5/1996 | Rubner et al. ............... | 427/259 |
| 5,527,925 A | * 6/1996 | Chabrecek et al. .......... | 549/430 |
| 5,529,727 A | 6/1996 | LaBombard ................ | 264/1.36 |
| 5,536,573 A | 7/1996 | Rubner ....................... | 428/378 |
| 5,807,636 A | 9/1998 | Sheu et al. .................. | 428/403 |
| 6,011,082 A | 1/2000 | Wang .......................... | 523/107 |

FOREIGN PATENT DOCUMENTS

| | | |
|---|---|---|
| EP | 0 032 443 A2 | 1/1981 |
| EP | 0 138 385 A2 | 9/1984 |
| EP | 0 989 418 A | 3/2000 |
| GB | 2 102070 | 1/1978 |
| JP | 01 158412 | 2/1980 |
| WO | WO 95/00618 | 1/1995 |
| WO | WO 95/02251 | 1/1995 |
| WO | WO 95/20407 | 8/1995 |
| WO | WO 96/37241 | 4/1996 |
| WO | WO 96/18498 | 6/1996 |
| WO | WO 96/31792 | 10/1996 |
| WO | WO 98/05269 A | 2/1998 |
| WO | WO 99/57581 A | 11/1999 |

OTHER PUBLICATIONS

Blood Capatibility–Surface Characteristic Relationships of a Langmuir–Blodgett Film Composed of an Anionic Amphiphile–Polycation Complex, Uchida M., et al., New Polymers Material, vol. 4, No. 3 pp. 119–211 (1994).
Enhancement of Light Emitting Diodes Based on Self–Assembled Heterosctructures of Poly (P–phenylene vinylene), O. Onitsuka, et al., Journal of Applied Physics, 80, (7), Oct. 1, 1996, ppg 4067–4071.
Investigations of New Self–Assembled Multilayer Thin Films Based on Alternately Absorbed Layers of Polyelectrolytes and Functional Dye Molecules, D. Yoo, et al., Material Resource, Soc. Symp. Proc. vol. 413, 1996, Materials Research Society.
New Electro–Active Self–Assembled Multilayer Thin Films Based on Alternately Absorbed Layers of Polyelectrolytes and Functional Dye Molecules, D. Yoo, et al., Elsevier Science, S.A., 1977, ppg 1425–1426.
Layer–By–Layer Modification of Surfaces Through the Use of Self–Assembled Monolayers of Polyions, D. Yoo, et al., ANTEC, 1995 ppg 2568–2570.
Molecular Self–Assembly of Conducting Polymers: A New Layer–by–Layer Think Film Deposition Process, J. H. Chung, et al.
Patterned Polymer Multilayer Fabrication by Controlled Adhesion of Polyelectrolytes to Plasma–Modified Fluoropolymer Surfaces, T. G. Vargo, et al, Supramolecular Science, vol. 2, Nos. 3–4, 1995, ppg 169–174.
Molecular–Level Processing of Conjugated Polymers 1. Layer–by–Layer Manipulation of Conjugated Polyions, M. Ferreira, et al., Macromolecules, vol. 28, No. 21, 1995, ppg 7107–7114.
Molecular–Level Processing of Conjugated Polymers 2. Layer–by–Layer Manipulation of In–Situ Polymerized p–type Doped Conduction Polymers, M. Ferreira, et al., Macromolecules, vol. 28, No. 21, 1995, ppg 7115–7120.
Molecular–Level Processing of Conjugated Polymers 3. Layer–by–Layer Manipulation of Polyaniline via Electrostatic Interactions, J. H. Cheung et al., Macromolecules, 1997, 30, ppg 2712–2716.
Abstract, JP 05318118, Matsumoto, Dec. 1993.

* cited by examiner

Primary Examiner—David J. Buttner
Assistant Examiner—Christopher Keehan
(74) Attorney, Agent, or Firm—Jian Zhou; Robert Gorman; R. Scott Meece

(57) ABSTRACT

The invention relates to a process for coating a material surface, comprising the steps of: (a) applying to the material surface a tie layer comprising a polyionic material; (b) covalently binding a bifunctional compound comprising an ethylenically unsaturated double b3nd to the tie layer; and (c) graft polymerizing a hydrophilic monomer onto the compound comprising the ethylenically unsaturated double bond. The coated articles that are obtainable by the process of the invention have desirable characteristics regarding adherences to the substrate, durability, hydrophilicity, wettability, biocompatibility and permeability and are thus useful for the manufacture of biomedical articles such as ophthalmic devices.

17 Claims, No Drawings

PROCESS FOR SURFACE MODIFYING SUBSTRATES AND MODIFIED SUBSTRATES RESULTING THEREFROM

CROSS-REFERENCE TO RELATED APPLICATION

This application claims the benefit of provisional application No. 60/228,022, filed Aug. 24, 2000.

FIELD OF THE INVENTION

The present invention generally relates to a method of modifying the surface of substrates such as contact lenses and other biomedical articles by at least partially coating the surfaces of such substrates with a reactive polymeric tie layer.

BACKGROUND OF THE INVENTION

Many devices used in biomedical applications require that the bulk of the device have one property and the surface of the device have a different property. For example, contact lenses may require relatively high oxygen permeability through the bulk of the lens to maintain good corneal health. However, materials that exhibit exceptionally high oxygen permeability (e.g. polysiloxanes) are typically hydrophobic and, untreated or not surface modified, will adhere to the eye. Thus a contact lens will generally have a core bulk material that is highly oxygen permeable and hydrophobic, and a surface that has been treated or coated to increase hydrophilic properties. This hydrophilic surface allows the lens to move relatively freely on the eye without adhering excessive amounts of tear lipid and protein.

A known method for modifying the hydrophilicity of a relatively hydrophobic contact lens material is through the use of a plasma treatment. Plasma treatment techniques are disclosed, for example, in PCT Publications Nos. WO 96/31793 to Nicolson et al., WO 99/57581 to Chabrecek et al., and WO 94/06485 to Chatelier et al. In the Chabrecek et al. application, photoinitiator molecules are covalently bound to the surface of the article after the article has been subjected to a plasma treatment which provides the surface with functional groups. A layer of polymerizable macromonomer is then coated onto the modified surface and heat or radiation is applied to graft polymerise the macromer to form the hydrophilic surface.

Plasma treatment processes, however, require a significant capital investment in plasma processing equipment. Moreover, plasma treatments take place in a vacuum and, thus, require that the substrate be mostly dry before exposure to the plasma. Thus, substrates, such as contact lenses, that are wet from prior hydration or extraction processes must be dried, thereby further adding to both the capital and production costs. As a result of the conditions necessary for plasma treatment, the incorporation of a plasma treatment process into an automated production process is extremely difficult.

Other methods of permanently altering the surface properties of polymeric biomaterials, such as contact lenses, have been developed. Some of these techniques include Langmuir-Blodgett deposition, controlled spin casting, chemisorptions, and vapor deposition. Examples of Langmuir-Blodgett layer systems are disclosed in U.S. Pat. Nos. 4,941,997; 4,973,429, and 5,068,318. Like plasma treatment, these techniques are not cost-effective methods that may easily be incorporated into automated production processes for making biomedical devices such as contact lenses.

A more recent technique developed for coating substrates is a layer-by-layer ("LbL") polymer absorption process, which is described, for example, in WO 99/35520 to Winterton at al., which concerns the absorption of polyionic compounds on "inert" materials.

SUMMARY OF THE INVENTION

Some of the shortcomings of the prior art are overcome with the present invention, which is directed to a method for modifying the surface of substrates, such as contact lenses and other biomedical articles, by at least partially coating the surfaces of such substrates with a reactive tie layer. The reactive polymeric tie layer, which is generally deposited onto the substrate surface as a polyelectrolytic layer, provides reactive sites for the attachment of, for example, a further hydrophilic polymer coating. In other words, the polymeric tie layer creates active moieties on the substrate surface trough functionalization of the surface by coating with a polyanion and/or polycation. Additional chemistry, such as condensation reactions, free radical-initiated polymerization reactions, and the like, can then be performed on these active moieties by reacting the moieties with various agents.

Various methods can be utilized to attach the reactive moieties of the polymeric tie layer to the substrate surface. One such method for creating the reactive sites is a layer-by-layer coating application that utilizes successive dips, sprays, or other applications of first a polyanionic layer, and then a polycationic layer. Additional polyelectrolytic layers may be applied by this successive application method. Another method applicable to the present invention is a single dip method that utilizes a bicomponent solution containing both a polycationic substance and a polyanionic substance in a single solution.

Among the various polyelectrolytes that can be utilized in such polymeric tie layer coating processes are polyacrylic acid and poly(allylamine hydrochloride). For example, a polyacrylic acid coating will provide carboxyl functional groups (—COOH) on the surface; and a poly(allylamine hydrochloride) coating will provide amino functional groups (—$NH_2$) on the surface. These reactive groups may then be further reacted with additional desired molecules or compounds such as functional monomers.

The present invention therefore in one aspect relates to a process for coating a material surface, comprising the steps of:
(a) applying to the material surface a tie layer comprising a polyionic material;
(b) covalently binding a bifunctional compound comprising an ethylenically unsaturated double bond to the tie layer; and
(c) graft polymerizing a hydrophilic monomer onto the compound comprising the ethylenically unsaturated double bond.

DETAILED DESCRIPTION OF REPRESENTATIVE EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield still a further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

The present invention is generally directed to the modification of a substrate surface by utilizing a method of coating the surface with various polyionic functional groups. The polycationic and/or polyanionic functional groups provide reactive sites to which various other chemical substances may be bound through traditional or non-traditional chemical reactions or attachment mechanisms.

In accordance with the present invention, a coating process is provided that can be utilized to deposit polyionic materials onto a substrate to form polymeric tie layers having functional groups thereon so that additional active agents can be attached thereto. In one embodiment, for example, a process of the present invention allows the deposition of a bicomponent polyionic solution to a biomaterial substrate, such as a contact lens.

In accordance with the present invention, a polyionic solution is employed to coat the substrate. In general, the polyionic solution contains at least one polycationic material and at least one polyanionic material, although more than one of each polyionic material can be employed. In one embodiment, for example, the polyionic solution is a bicomponent solution containing a polycation and a polyanion.

Typically, a polycationic material of the present invention can include any material known in the art to have a plurality of positively charged groups along a polymer chain, such as a poly(allylamine hydrochloride). Likewise, a polyanionic material of the present invention can typically include any material known in the art to have a plurality of negatively charged groups along a polymer chain, such as polyacrylic acid.

According to one embodiment of the present invention, a polycationic material is combined with a polyanionic material to form a "single-dip" polyionic solution. In general, the polyionic components are added in non-stoichometric amounts such that one of the components is present within the solution in a greater amount than another component of opposite charge. In particular, the molar charge ratio, as defined herein, can be from about 3:1 to about 100:1. In certain embodiments, the molar charge ratio is 10:1 (polyanion:polycation).

Layers of polyionic components can be coated onto the substrate. For example, in one embodiment, polyanionic-polycationic-polyanionic alternating repeating layers are assembled when the substrate is dipped into the solution.

Besides containing polyionic components, a polyionic solution of the present invention can also contain various other materials. For example, the polyionic solution can contain antimicrobials, antibacterials, radiation-absorbing materials, cell growth inhibitors, etc.

In other embodiments, the substrate can be dipped sequentially into separately charged polyionic solutions. In these embodiments, a solution of polycationic material may be the first stage dip and a solution of polyanionic material may be the second stage dip (or vice versa). Additional polyionic materials may be utilized.

In general, a surface modified device of the present invention can be made from various materials. Examples of suitable substrate materials include quartz, ceramics, glasses, silicate materials, silica gels, metals, metal oxides, carbon materials such as graphite or glassy carbon, natural or synthetic organic polymers, or laminates, composites or blends of such materials, including natural or synthetic organic polymers or modified biopolymers which are well-known. Examples of polymers include polyaddition and polycondensation polymers (polyurethanes, epoxy resins, polyethers, polyesters, polyamides and polyimides); vinyl polymers (polyacrylates, polymethacrylates, polyacrylamides, polymethacrylamides, polystyrene, polyethylene and halogenated derivatives thereof, polyvinylacetate and polyacrylonitrile); or elastomers (silicones, polybutadiene and polyisoprene).

A particular group of bulk materials from which the inventive substrates may be formed comprises organic polymers selected from polyacrylates, polymethacrylates, poly (N,N-dimethylacrylamides), polymethacrylamides, polyvinyl acetates, polysiloxanes, perfluoroalkyl polyethers, fluorinated polyacryalates or -methacrylates and amphiphilic segmented copolymers comprising at least one hydrophobic segment, for example a polysiloxane or perfluoroalkyl polyether segment or a mixed polysiloxane/perfluoroalkyl polyether segment, and at least one hydrophilic segment, for example a polyoxazoline, poly(2-hydroxyethylmethacrylate), polyacrylamide, poly(N,N-dimethylacrylamide), polyvinylpyrrolidone polyacrylic or polymethacrylic acid segment or a copolymeric mixture of two or more of the underlying monomers.

A preferred group of materials to be coated are those being conventionally used for the manufacture of biomedical devices, e.g. contact lenses, in particular contact lenses for extended wear, which are not hydrophilic per se. Such materials are known to the skilled artisan and may comprise for example polysiloxanes, perfluoroalkyl polyethers, fluorinated poly(meth)acrylates or equivalent fluorinated polymers derived e.g. from other polymerizable carboxylic acids, polyalkyl (meth)acrylates or equivalent alkylester polymers derived from other polymerizable carboxylic acids, or fluorinated polyolefines, such as fluorinated ethylene or propylene, for example tetrafluoroethylene, preferably in combination with specific dioxols, such as perfluoro-2,2-dimethyl-1,3-dioxol. Examples of suitable bulk materials are e.g. Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

Another group of preferred materials to be coated is amphiphilic segmented copolymers comprising at least one hydrophobic segment and at least one hydrophilic segment which are linked through a bond or a bridge member. Examples are silicone hydrogels, for example those disclosed in PCT applications WO 96/31792 to Nicolson et al. and WO 97/49740 to Hirt et al.

A particular preferred group of bulk materials comprises organic polymers selected from polyacrylates, polymethacrylates, polyacrylamides, poly(N,N-dimethylacrylamides), polymethacrylamides, polyvinyl acetates, polysiloxanes, perfluoroalkyl polyethers, fluorinated polyacrylates or -methacrylates and amphiphilic segmented copolymers comprising at least one hydrophobic segment, for example a polysiloxane or perfluoroalkyl polyether segment or a mixed polysiloxane/perfluoroalkyl polyether segment, and at least one hydrophilic segment, for example a polyoxazoline, poly(2-hydroxyethylmethacrylate), polyacrylamide, poly(N,N-dimethylacrylamide), polyvinylpyrrolidone polyacrylic or polymethacrylic acid segment or a copolymeric mixture of two or more of the underlying monomers.

The material to be coated may also be any blood-contacting material conventionally used for the manufacture of renal dialysis membranes, blood storage bags, pacemaker leads or vascular grafts. For example, the material to be modified on its surface may be a polyurethane, polydimethylsiloxane, polytetrafluoroethylene, polyvinylchloride, Dacron™ or Silastic™ type polymer, or a composite made therefrom.

Moreover, the material to be coated may also be an inorganic or metallic base material without suitable reactive groups, e.g. ceramic, quartz, or metals, such as silicon or gold, or other polymeric or non-polymeric substrates. E.g. for implantable biomedical applications, ceramics are very useful. In addition, e.g. for biosensor purposes, hydrophilically coated base materials are expected to reduce nonspecific binding effects if the structure of the coating is well controlled. Biosensors may require a specific carbohydrate coating on gold, quartz, or other non-polymeric substrates.

The form of the material to be coated may vary within wide limits. Examples are particles, granules, capsules, fibers, tubes, films or membranes, preferably moldings of all kinds such as ophthalmic moldings, for example intraocular lenses, artificial cornea or in particular contact lenses.

Suitable substances that may be utilized to form the polymeric tie layer of the present invention include various polyionic materials. One such suitable layer may be formed from a first and second ionic polymer having opposite charges, wherein the "first ionic polymer" indicates the polymer that is first of all applied to the article surface, and the "second ionic polymer" indicates the polymer that is applied to the article surface after it has already been modified with the first ionic polymer. The bulk material may comprise as the tie layer one or more than one such polymeric layers. For example, from 1 to 50 layers containing the same or different ionic polymers in each case, from 1 to 25 layers, from 1 to 20 layers, from 1 to 10 layers, from 1 to 5 layers, or just one layer may be utilized to form the tie layer.

In addition, it may be desirous to have only partial tie layer coverage on the article being treated so that an incomplete tie layer is formed. This may be particularly helpful if only one side of the article needs to be surface modified or if it is desirous to have the two sides of, for example, a contact lens, to have two different coatings—one for the front of the lens and one for the cornea side of the lens.

The polyionic materials that may be employed in the present tie layer include polyanionic and polycationic polymers. Examples of suitable anionic polymers include, for example, a synthetic polymer, a biopolymer or modified biopolymer comprising carboxy, sulfo, sulfato, phosphono or phosphato groups or a mixture thereof, or a salt thereof, for example, a biomedical acceptable salt and especially an ophthalmically acceptable salt thereof when the substrate to be coated is an ophthalmic device.

Examples of synthetic anionic polymers are: a linear polyacrylic acid (PAA), a branched polyacrylic acid, for example a Carbophil® or Carbopol® type from Goodrich Corp., a polymethacrylic acid (PMA), a polyacrylic acid or polymethacrylic acid copolymer, for example a copolymer of acrylic or methacrylic acid and a further vinylmonomer, for example acrylamide, N,N-dimethyl acrylamide or N-vinylpyrrolidone, a maleic or fumaric acid copolymer, a poly(styrenesulfonic acid) (PSS), a polyamido acid, for example a carboxy-terminated polymer of a diamine and a di- or polycarboxylic acid, for example carboxy-terminated Starburst™ PAMAM dendrimers (Aldrich), a poly(2-acrylamido-2-methylpropanesulfonic acid) (poly-(AMPS)), or an alkylene polyphosphate, alkylene polyphosphonate, carbohydrate polyphosphate or carbohydrate polyphosphonate, for example a teichoic acid.

Examples of anionic biopolymers or modified biopolymers are: hyaluronic acid, glycosaminoglycanes such as heparin or chondroitin sulfate, fucoidan, poly-aspartic acid, poly-glutamic acid, carboxymethyl cellulose, carboxymethyl dextranes, alginates, pectins, gellan, carboxyalkyl chitins, carboxymethyl chitosans, sulfated polysaccharides.

A preferred anionic polymer is a linear or branched polyacrylic acid or an acrylic acid copolymer. A more preferred anionic polymer is a linear or branched polyacrylic acid. A branched polyacrylic acid in this context is to be understood as meaning a polyacrylic acid obtainable by polymerizing acrylic acid in the presence of suitable (minor) amounts of a di- or polyvinyl compound.

A suitable cationic polymer as part of the bilayer is, for example, a synthetic polymer, biopolymer or modified biopolymer comprising primary, secondary or tertiary amino groups or a suitable salt thereof, preferably an ophthalmically acceptable salt thereof, for example a hydrohalogenide such as a hydrochloride thereof, in the backbone or as substituents. Cationic polymers comprising primary or secondary amino groups or a salt thereof are preferred.

Examples of synthetic cationic polymers are:
(i) a polyallylamine (PAH) homo- or copolymer, optionally comprising modifier units;
(ii) a polyethyleneimine (PEI);
(iii) a polyvinylamine homo- or copolymer, optionally comprising modifier units;
(iv) a poly(vinylbenzyl-tri-$C_1$–$C_4$-alkylammonium salt), for example a poly(vinylbenzyl-tri-methyl ammoniumchloride);
(v) a polymer of an aliphatic or araliphatic dihalide and an aliphatic N,N,N',N'-tetra-$C_1$–$C_4$-alkyl-alkylenediamine, for example a polymer of (a) propylene-1,3-dichloride or -dibromide or p-xylylene dichloride or dibromide and (b) N,N,N',N'-tetramethyl-1,4-tetramethylene diamine;
(vi) a poly(vinylpyridine) or poly(vinylpyridinium salt) homo- or copolymer;
(vii) a poly (N,N-diallyl-N,N-di-$C_1$–$C_4$-alkyl-ammoniumhalide) comprising units of formula:

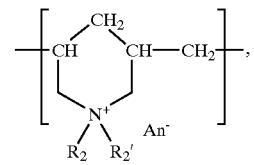

wherein $R_2$ and $R_2'$ are each independently $C_1$–$C_4$-alkyl, in particular methyl, and $An^-$ is a, for example, a halide anion such as the chloride anion;
(viii) a homo- or copolymer of a quaternized di-$C_1$–$C_4$-alkyl-aminoethyl acrylate or methacrylate, for example a poly(2-hydroxy-3-methacryloylpropyltri-$C_1$–$C_2$-alkylammonium salt) homopolymer such as a a poly(2-hydroxy-3-methacryloylpropyltri-methylammonium chloride), or a quaternized poly(2-dimethylaminoethyl methacrylate or a quaternized poly(vinylpyrrolidone-co-2-dimethylaminoethyl methacrylate);
(ix) POLYQUAD® as disclosed in EP-A-456,467; or
(x) a polyaminoamide (PAMAM), for example a linear PAMAM or a PAMAM dendrimer such as an amino-terminated Starburst™ PAMAM dendrimer (Aldrich).

The above mentioned polymers comprise in each case the free amine, a suitable salt thereof, for example a biomedically acceptable salt or in particular an ophthalmically acceptable salt thereof, as well as any quaternized form, if not specified otherwise.

Suitable comonomers optionally incorporated in the polymers according to (i), (iii), (vi) or (viii) above are, for example, hydrophilic monomers such as acrylamide, methacrylamide, N,N-dimethyl acrylamide, N-vinylpyrrolidone and the like.

Suitable modifier units of the polyallylamine (i) are known, for example from WO 00/31150 and comprise, for example, units of formula:

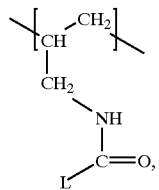

(1)

wherein L is $C_2$–$C_6$-alkyl which is substituted by two or more same or different substituents selected from the group consisting of hydroxy, $C_2$–$C_5$-alkanoyloxy and $C_2$–$C_5$-alkylaminocarbonyloxy.

Preferred substituents of the alkyl radical L are hydroxy, acetyloxy, propionyloxy, methylaminocarbonyloxy or ethylaminocarbonyloxy, especially hydroxy, acetyloxy or propionyloxy and in particular hydroxy.

L is preferably linear $C_3$–$C_6$-alkyl, more preferably linear $C_4$–$C_5$-alkyl, and most preferably n-pentyl, which is in each case substituted as defined above. A particularly preferred radical L is 1,2,3,4,5-pentahydroxy-n-pentyl.

Examples of cationic biopolymers or modified biopolymers that may be employed in the tie layer of the present invention include: basic peptides, proteins or glucoproteins, for example, a poly-ε-lysine, albumin or collagen, aminoalkylated polysaccharides such as a chitosan or aminodextranes.

Particular cationic polymers for forming the polymer tie layer that are attached to the bulk material of the present invention include a polyallylamine homopolymer; a polyallylamine comprising modifier units of the above formula (1); a polyvinylamine homo- or -copolymer or a polyethyleneimine homopolymer, in particular a polyallylamine or polyethyleneimine homopolymer, or a poly(vinylamine-co-acrylamid) copolymer.

In addition to polyionic materials, a solution forming the tie layer or part of it, can also contain additives. As used herein, an additive can generally include any chemical or material. For example, active agents, such as antimicrobials and/or antibacterials can be added to a solution forming the tie layer, particularly when used in biomedical applications. Some antimicrobial polyionic materials include polyquaternary ammonium compounds, such as those described in U.S. Pat. No. 3,931,319 to Green et al. (e.g. POLYQUAD®).

Moreover, other examples of materials that can be added to a solution forming the tie layer are polyionic materials useful for ophthalmic lenses, such as materials having radiation absorbing properties. Such materials can include, for example, visibility tinting agents, iris color modifying dyes, and ultraviolet (UV) light tinting dyes.

Still another example of a material that can be added to a solution forming the tie layer is a polyionic material that inhibits or induces cell growth. Cell growth inhibitors can be useful in devices that are exposed to human tissue for an extended time with an ultimate intention to remove (e.g. catheters or Intra Ocular Lenses (IOL's), where cell overgrowth is undesirable), while cell growth-inducing polyionic materials can be useful in permanent implant devices (e.g. artificial cornea).

When additives are applied to a solution forming the tie layer, such additives, preferably, have a charge. By having a positive or negative charge, the additive can be substituted for one of the polyionic materials in solution at the same molar ratio. For example, polyquaternary ammonium compounds typically have a positive charge. As such, these compounds can be substituted into a solution of the present invention for the polycationic component such that the additive is applied to a substrate material in a manner similar to how a polycationic would be applied.

It should be understood, however, that non-charged additives can also be applied to a substrate material of the present invention. For example, in one embodiment, a polycationic layer can first applied onto a substrate material. Thereafter, a non-charges additive can be applied and immediately entrapped by a polyanionic material applied thereon. In this embodiment, the polyanionic material can sufficiently entrap the non-charged additive between two or more layers of polyionic material. After such entrapment, the substrate material can then be coated with other layers of polyionic materials in accordance with the present invention.

As discussed above, a solution forming the tie layer can generally be formed from polyionic materials and various other chemicals. In one embodiment, a solution forming the tie layer is a single component system that contains either a cationic or an anionic material that is employed in successive applications. In another embodiment, a solution forming the tie layer can be a single-application, bicomponent solution that contains at least one polycationic and one polyanionic material. In other embodiments, the solution forming the tie layer can contain more than two components of polyionic materials, such as 3, 4, 5, or more components.

Regardless of the number of polyionic components present within a single-application, in a bicomponent solution forming the tie layer, it is typically desired that one of the polyionic components of the solution be present in a greater amount than another component such that a non-stoichometric solution can be formed. For example, when a polyanionic/polycationic bicomponent solution is formed, either one of the components can be present in an amount greater than the other component. By forming a solution from polyionic materials in such a manner, a substrate material can be suitably coated with the tie layer solution in a single dip.

To control the amount of each polyionic component within a single-application, bicomponent solution forming the tie layer, the "molar charge ratio" can be varied. As used therein, "molar charge ratio" is defined as the ratio of charged molecules in solution on a molar basis. For example, a 10:1 molar charge ratio can be defined as 10 molecules of a polyanion to 1 molecule of a polycation, or 10 molecules of a polycation to 1 molecule of a polyanion. The molar charge ratio can be determined as defined above for any number of components within a solution, as long as at least one polycation and one polyanion are included therein.

As the molar charge ratio is substantially increased, the structure of the tie layer on a particular substrate can become more "open". In some instances, such an opening of the tie layer structure can result in the requirement of more dipping steps to achieve the desired tie layer structure of the substrate material. In this regard, a solution forming the tie layer typically has a "molar charge ratio" of about 3:1 to about 100:1. In one embodiment, the solution forming the tie layer has a molar charge ratio of about 5:1 (polyanion:polycation). In another embodiment, the solution forming the tie layer has a molar charge ratio of about 1:5 (polyanion:polycation). In still another embodiment, a 3:1 or 1:3 molar charge ratio may be utilized.

In a certain embodiment, the solution forming the tie layer has a molar charge ratio of about 10:1 (polyanion:polycation). By employing a solution forming the tie layer having a predominant amount of polyanionic material, a substrate material can be coated in a manner such that the outer layer is a polyanionic material. Substrates having an outer polyanionic material are typically more acidic. It is believed that in some applications, an acidic outer layer can provide a more hydrophilic substrate and allow better wetting, thus allowing hydrophilic coating agents to approach the substrate more intimately. This allows the process to proceed more rapidly. However, it should be understood that an outer layer of polycationic material may also be desirable. In contrast to a polyanionic outer tie layer, a polycationic outer tie layer can be achieved by providing a tie layer solution that contains a predominant amount of polycationic material.

In accordance with the present invention, a solution forming the tie layer, whether a single component solution for sequential dipping or a multi-component for single dipping, the pH level is typically maintained such that the solution remains stable. When the pH of the solutions forming the tie layer is improperly varied, a salt can sometimes form trough back-titration. Such precipitation can often have an adverse affect on the ability of the tie layer solution to coat the substrate layer as desired. As such, depending on the particular solution used, the pH of the solution is normally maintained at a value within about ±0.5 of the appropriate pH range from the solution. In certain embodiments, the pH of the solution forming the tie layer is maintained at a pH of ±0.1 of the appropriate pH range for the solution. By maintaining the pH of the solution within a specified range of the appropriate pH for the solution, precipitation can be substantially inhibited.

The appropriate pH range for a solution forming the tie layer can vary depending on the particular polyionic materials chosen. Any suitable method known in the art can be utilized to determine the appropriate pH range for a given solution. One such method is described in "Controlling Bilayer Composition and Surface Wettability of Sequentially Adsorbed Multilayers of Weak Polyelectrolytes" by Dongsik Yoo, Seimel S. Shiratori, and Michael R. Rubner, which is published in MACROMOLECULES® Volume 31, number 13, pages 4309–4318 (1989). For example, in a particular embodiment for multi-component solutions forming the tie layer, a 10:1 (polyanion:polycation) ratio of polyacrylic acid and poly(allylamine hydrochloride) is utilized. For this particular bicomponent solution forming the tie layer, the appropriate pH range was determined to be about 2.5.

The formation and the application of layers forming the tie layer onto the substrate surface may be accomplished according to various processes. For example, the substrate material may be immersed in a solution containing both an anionic polymer(s) and a cationic polymer(s), or one or more layers each of the anionic polymer(s) and cationic polymer(s) are successively deposited on the substrate material surface, for example by dipping, spraying, printing, spreading, pouring, rolling, spin coating or vacuum vapour deposition, spraying or particularly dipping being preferred. Following the deposition of one ionic polymer the bulk material may be rinsed or dried before the deposition of the next ionic polymer having opposite charges.

One particular dip method involves the steps of (i) applying a layer of a first ionic polymer, for example of a cationic or an anionic polymer to the bulk substrate material by immersing the bulk material in a solution of the first ionic polymer; (ii) optionally, rinsing the bulk material by immersing it in a rinsing solution; (iii) optionally, drying said bulk material; and (iv) applying a layer of a second ionic polymer having charges opposite of the charges of the first ionic polymer, for example an anionic or a cationic polymer, to the bulk material by immersing the bulk material in a solution of the second ionic polymer.

A further dip method involves immersing the bulk material in a multi-component solution comprising both the anionic and cationic polymer.

Whether a single component solution for sequential dipping or a multi-component for single dipping of the present invention, the dip solutions of the present invention generally comprise the respective polymer diluted in one or more different solvents. Suitable solvents are, for example, water or an aqueous solution comprising a water-miscible organic solvent, for example a $C_1$–$C_4$-alkanol such as methanol or ethanol; the preferred solvent is pure water. The aqueous solutions of the cationic or anionic polymer advantageously each have a slight acidic pH value, for example a pH from about 2 to about 5 and preferably from about 2.5 to about 4.5. The concentrations of the dip solutions may vary within wide limits depending, for example, on the particular ionic polymer involved or the desired thickness. However, it may generally be preferred to formulate relatively dilute solutions of the ionic polymers. A particular anionic or cationic polymer concentration is from about 0.0001 to about 0.25 weight percent, from about 0.0005 to about 0.15 weight percent, from about 0.001 to about 0.25 weight percent, from about 0.005 to about 0.01 weight percent, from about 0.01 to about 0.05 weight percent and, in particular, from 0.001 to 0.1 percent by weight, relative to the total weight of the solution.

A suitable rinsing solution may be an aqueous solution. The aqueous solution may have a pH of about 2 to about 7, from about 2 to about 5, or from about 2.5 to about 4.5.

Partial drying or removal of excess rinsing solution from the surface between solution applications may be accomplished by a number of means known in the art. While the bulk material may be partially dried by merely allowing the coated material to remain in an air atmosphere for a certain period of time, the drying time may be accelerated by application of a mild stream of air to the surface. The flow rate may be adjusted as a function of strength of the material being dried and the mechanical fixturing of the material.

The thickness of the tie layer may be adjusted during the formation process by addition of one or more salts, such as sodium chloride to the ionic polymer solution. A particular salt concentration that may be employed is about 0.1 to about 2.0 weight percent. As the salt concentration is increased, the polyionic material takes on a more globular conformation. However, if the concentration is raised to high, the polyionic material will not deposit well, if at all, on the substrate surface.

The polymeric tie layer formation process may be repeated a plurality of times, for example from 1 to about 50 times, from 1 to about 24 times, from 1 to about 14 times, or only one time.

The immersion time for each of the coating and optional rinsing steps may vary depending on a number of factors. In general, a rinsing time of from about 30 seconds to about 30 minutes, from about 1 to about 20 minutes, from about 1 to about 6 minutes may be employed. The immersion in the polymer solutions may take place at various temperatures, such as at room temperature or at a lower temperature.

Instead of coating the substrate material by means of a dip technique, the substrate may be coated using spray coating techniques. The above given conditions and features concerning solvents, concentrations, presence of salts, pH, temperature, number and sequence of coating steps, and rinsing or drying steps apply accordingly. Spray coating technique in this context comprises any known process in the art including, for example, conventional techniques of applying a fluid, or techniques using ultrasonic energy, or electrostatic spray coating techniques. In addition, a mixture of dip and spray techniques may also be employed.

In this regard, an embodiment of the single-application, bicomponent solution forming the tie layer can be prepared as follows. However, it should be understood that the following description is for exemplary purposes only and that a tie layer solution of the present invention can be prepared by other suitable methods.

A bicomponent solution forming the tie layer can be prepared by first dissolving a single component polyanionic material in water or other solvent at a designated concentration. For example, in one embodiment, a solution of polyacrylic acid (PAA) having a molecular weight of about 90,000 is prepared by dissolving a suitable amount of the material in water to form a 0.001 M PAA solution. Once dissolved, the pH of the polyanionic solution can be properly adjusted by adding a basic or acidic material. In the embodiment above, for example, a suitable amount of 1N hydrochloric acid (HCl) can be added to adjust the pH to 2.5.

After preparing the polyanionic solution, the polycationic solution can be similarly formed. For example, in one embodiment, poly(allylamine hydrochloride) (PAH) having a molecular weight of about 50,000 to about 65,000 can be dissolved in water to form a 0.001M solution. Thereafter, the pH can be similarly adjusted to 2.5 by adding a suitable amount of hydrochloric acid.

The above solutions can then be mixed to form a single-dip solution for forming the tie layer of the present invention. In one embodiment, for example, the solutions can be mixed slowly to obtain the solution forming the tie layer. The amount of each solution applied if the mix depends on the molar charge ratio desired. For example, if a 10:1 (polyanion:polycation) solution is desired, 1 part (by volume) of the PAH solution can be mixed into 10 parts of the PAA solution. After mixing, the solution can also be filtered if desired.

Once the solution forming the tie layer is formed in accordance with the present invention, it can then be applied to a substrate material by any of the methods described above.

In some embodiments of the present invention, the particular substrate material utilized can also be "preconditioned" or "oriented" before being dipped into solution forming the tie layer. Although not required, preconditioning the substrate material in accordance with the present invention can enhance the growth of polyionic layers in the "single dip" type process. In particular, pre-conditioning a substrate material typically involves increasing the roughness of the substrate surface.

In this regard, the roughness of the substrate surface can be altered in a variety of ways. Generally, an "underlayer" or "primer layer" of tie layer solution can be initially applied to the substrate material to accomplish the desired surface alteration. For example, in one embodiment, one or more standard layer-by-layer dip coatings can be employed as an underlayer for the ultimate dip coating of the present invention. The "underlayer" can be applied by any method known in the art, such as by spray coating, dipping, etc. In some embodiments, the underlayer can be made from a polyionic material, such as poly(ethyleneimine). After applying this primer coating or underlayer, in one embodiment, the substrate can then be dipped into the ultimate coating solution. For instance, in one embodiment, the ultimate coating solution can contain poly(allylamine hydrochloride) and polyacrylic acid. In still another embodiment, the solution forming the tie layer can contain poly(allylamine hydrochloride) and sodium poly(styrene sulfonate).

Moreover, in another embodiment, the substrate material can be allowed to swell in a solvent solution containing a solvent and at least one polyionic component. In general, any solvent that can allow the components within the solution to remain stable in water is suitable for use in the present invention. Examples of suitable alcohols can include, but are not limited to, isopropyl alcohol, hexanol, ethanol, etc. In certain embodiments, the substrate material is first allowed to swell in an alcohol solution containing about 20% isopropyl alcohol and about 80% water. In some embodiments, the alcohol solution used to swell the substrate can also be used as the solvent in the ultimate single-dip polyionic tie layer solution.

After swelling, the substrate material can then be removed from the solvent solution and allowed to "shrink". This "shrinking" step causes the substrate material to entrap part or all of the initial layer of the polycation or polyanion present within the solvent solution. The swelling/entrapment process described in this embodiment can enhance the ability of the solution forming the tie layer to coat the substrate material.

However, it may often be desired to apply a tie layer having a substantial thickness that cannot be sufficiently applied with a single dip. For example, in one embodiment of the present invention, a 500 angstrom tie layer (as measured by atomic force microscopy ("AFM")) is applied to a substrate material in two dipping steps. In particular, a 10:1. polyanion to polycation dip is first applied to the substrate material. Thereafter, a 1:10 polyanion to polycation dip is employed as a second layer. In some embodiments, more than two dips, such as 3 to 5 dips in multi-component solutions of the present invention can be utilized. For example, when coating a contact lens material according to the present invention, three dips may be utilized.

The molecular weight of the anionic and cationic polymers used to prepare the tie layers may vary within wide limits depending on the desired characteristics such as adhesion on the bulk material, coating thickness and the like. Generally, as the molecular weight of the polyionic materials increases, the tie layer thickness increases. However, if the increase in molecular weight is too substantial, the difficulty in handling may also increase. In general, a weight average molecular weight of from about 5,000 to about 5,000,000, preferably from about 10,000 to 1,000,000, more preferably from 15,000 to 500,000, even more preferably from 20,000 to 200,000 and in particular from 40,000 to 150,000, has proven as valuable both for the anionic and cationic polymer(s) forming the tie layer.

According to the above-mentioned methods, substrate materials are obtained that comprise a tie layer of one or more polyelectrolytes absorbed onto and/or heteropolarly bound on the surface. Due to this modification, the surface is provided with functional groups such as, for example, carboxy, sulfone, sulfato, phosphono or phosphate groups or primary, secondary or tertiary amine groups. It is these functional groups that may be further reacted with various agents to form the surface-modified substrates of the present invention.

According to step (b) of this invention bifunctional compounds comprising an ethylenically unsaturated double bond are covalently bound to the tie layer.

Bifunctional compounds comprising a polymerizable carbon-carbon double bond to be coupled with functional groups of the tie layer are, for example, compounds of formula:

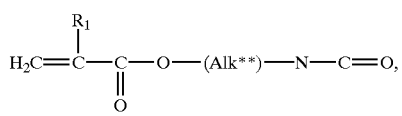

(2a)

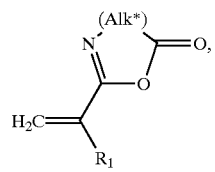

(2b)

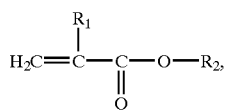

(2c)

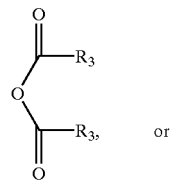

(2d)

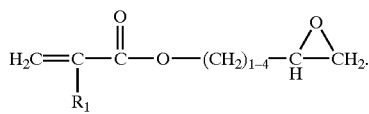

(2e)

wherein $R_1$ is hydrogen, $C_1$–$C_4$-alkyl or halogen;
$R_2$ is hydrogen, unsubstituted or hydroxy-substituted $C_1$–$C_6$-alkyl or phenyl;
$R_3$ and $R_3'$ are each an ethylenically unsaturated radical having from 2 to 6 C-atoms, or $R_3$ and $R_3'$ together form a bivalent radical —C($R_4$)=C($R_4'$)— wherein $R_4$ and $R_4'$ are each independently of the other hydrogen, $C_1$–$C_4$-alkyl or halogen; and
(Alk*) is $C_1$–$C_6$-alkylene, and (Alk**) is $C_2$–$C_{12}$-alkylene.

The following preferences apply to the variables contained in formulae (2a)–(2e):
$R_1$ is preferably hydrogen or $C_1$–$C_4$-alkyl, in particular hydrogen or methyl.
$R_2$ is preferably hydrogen or hydroxy-$C_1$–$C_4$-alkyl, in particular hydrogen or β-hydroxyethyl.
$R_3$ and $R_3'$ are preferably each vinyl or 1-methylvinyl, or $R_3$ and $R_3'$ together form a radical —C($R_4$)=C($R_4'$)—; wherein $R_4$ and $R_4'$ are each independently hydrogen or methyl.

(Alk*) is preferably methylene, ethylene or 1,1-dimethyl-methylene, in particular a radical —$CH_2$— or —$C(CH_3)_2$—.
(Alk**) is preferably $C_2$–$C_4$-alkylene and in particular 1,2-ethylene.

Preferred vinyl monomers having a reactive group are 2-isocyanatoethylmethacrylate (IEM), 5,5-dimethyl-2-vinyl-oxazolin-4-one, acrylic acid, methacrylic acid, acrylic anhydride, maleic acid anhydride, 2-hydroxyethylacrylate (HEA), 2-hydroxyethylmethacrylate (HEMA), glycidylacrylate or glycidylmethacrylate, particularly preferred is 2-isocyanatoethylmethacrylate (IEM).

The method of attaching a bifunctional compound of formula (2a)–(2e) to the tie layer depends on the nature of the reactive groups being present in compounds (2a)–(2e) and at the surface of the tie layer.

In case that a compound of formula (2a) has to be coupled to a tie layer containing amino or hydroxy groups, the reaction may be carried out in an inert organic solvent such as acetonitrile, an optionally halogenated hydrocarbon, for example petroleum ether, methylcyclohexane, toluene, chloroform, methylene chloride and the like, or an ether, for example diethyl ether, tetrahydrofurane, dioxane, or a more polar solvent such as DMSO, DMA, N-methylpyrrolidone or even a lower alcohol or water, at a temperature of from 0 to 100° C., preferably from 0 to 50° C. and particularly preferably at room temperature, optionally in the presence of a catalyst, for example a tertiary amine such as triethylamine or tri-n-butylamine, 1,4-diazabicyclooctane, or a tin compound such as dibutyltin dilaurate or tin dioctanoate. In addition, the reaction of the isocyanato groups with amino groups may also be carried out in an aqueous solution in the absence of a catalyst. It is advantageous to carry out the above reactions under an inert atmosphere, for example under a nitrogen or argon atmosphere.

In case that a compound of formula (2a) has to be coupled to the surface of a tie layer containing amino groups, the reaction may be carried out advantageously at room temperature or at elevated temperature, for example at about 20 to 75° C., in water, in a suitable organic solvent or mixtures thereof, for example in an aqueous medium or in an aprotic polar solvent such as DMF, DMSO, dioxane, acetonitrile and the like.

In case that a compound of formula (2b) has to be coupled to the surface of a bulk material or to a natural or synthetic polymer containing hydroxy groups, aprotic polar solvents are preferred.

In case that a carboxy compound of formula (2c) has to be coupled to a tie layer containing amino or hydroxy groups, or a hydroxy compound of formula (2c) with carboxy groups of the surface, the reaction may be carried out under the conditions that are customary for ester or amide formation. It is preferred to carry out the esterification or amidation reaction in the presence of an activating agent, for example N-ethyl-N'-(3-dimethyl aminopropyl)-carbodiimide (EDC), N-hydroxy succinimide (NHS) or N,N'-dicyclohexyl carbodiimide (DCC).

In case that a compound of formula (2d) has to be coupled to a tie layer containing amino or hydroxy groups, the reaction may be carried out as described in organic textbooks, for example in an aprotic solvent, for example one of the above-mentioned aprotic solvents, at a temperature from room temperature to about 100° C.

In case that a compound of formula (2e) has to be coupled to a tie layer containing amino or hydroxy groups, the reaction may be carried out, for example, at room temperature or at elevated temperature, for example at about 20 to 100° C., in an aprotic medium using a base catalyst, for example, Al(O—$C_1$–$C_6$-alkyl)$_3$ or Ti(O—$C_1$–$C_6$-alkyl)$_4$.

The coating obtainable by steps (a) and (b) constitutes a "primary coating" to which a "secondary coating" is attached in step (c). In step (c), a hydrophilic monomer or a mixture of hydrophilic monomers is graft polymerized onto the ethylenically unsaturated double bonds introduced in step (b).

In this invention, the expression "hydrophilic monomer" is understood to mean a monomer that typically produces as homopolymer a polymer that is water-soluble or capable of absorbing at least 10% by weight water.

The hydrophilic monomers may be applied to the material surface and polymerized there according to various known processes. For example, the modified bulk material is immersed in a solution of the hydrophilic monomer(s), or a layer of the monomer(s) is first of all deposited on the modified bulk material surface, for example by dipping, spraying, spreading, knife coating, pouring, rolling, spin coating or vacuum vapor deposition. Preferably, a solution of the hydrophilic monomer(s) in a suitable solvent, e.g. water, or in a mixture of polar solvents is used.

Suitable hydrophilic monomers include, without the following being an exhaustive list, hydroxy-substituted $C_1$–$C_2$-alkylacrylates, acrylic acid, acrylamide, methacrylamide, N-mono or N,N-di-$C_1$–$C_2$-alkylacrylamide and methacrylamide, ethoxylated acrylates and methacrylates, hydroxy-substituted $C_1$–$C_2$-alkyl vinyl ethers, sodium ethylenesulfonate, sodium styrenesulfonate, 2-acrylamido-2-methylpropanesulfonic acid, N-vinyl-pyrrole, N-vinylsuccinimide, five- to seven-membered N-vinyl lactams, 2- or 4-vinylpyridine, amino- (the term "amino" also including quaternary ammonium), mono-$C_1$–$C_2$-alkylamino- or di-$C_1$–$C_2$-alkylamino-$C_1$–$C_2$-alkyl acrylates and methacrylates, allyl alcohol and the like. Preferred hydrophilic monomers are acrylamide, acrylic acid, methacrylic acid, hydroxyethyl methacrylate, hydroxyethyl acrylate, methacrylamide, N,N-dimethylacrylamide, allylalcohol, N-vinylpyrrolidone and N,N-dimethylaminoethyl acrylate.

Suitable polymerization initiators are known to the skilled artisan and comprise, for example, persulfates, peroxides, hydroperoxides, azo-bis(alkyl- or cycloalkylnitriles), percarbonates or mixtures thereof. The use of persulfates is preferred.

After the polymerization, any non-covalently bound components, e.g. non-reacted monomer(s), can be removed, for example by treatment with suitable solvents.

It is believed that the grafts of one or more monomers in step (c) create a so-called brush structure comprising a plurality of polymer chains, which are covalently bound to the tie layer.

An additional valuable embodiment of the present invention is provided, if in step (c) a hydrophilic monomer comprising a reactive group, optionally in admixture with a further monomer, is used.

In this embodiment, after the polymerization step according to (c),
(i) the reactive groups of the polymer chains may be reacted with a further compound of formula (2a)–(2e) comprising an ethylenically unsaturated double bond, followed by the
(ii) graft polymerization of a hydrophilic monomer and optionally a co-monomer having a crosslinkable group onto the ethylenically unsaturated double bond, and
(iii) in case crosslinkable groups being present in step (ii), crosslinking of said groups is initiated.

Hydrophilic monomers to be used in step (ii) comprise the same as used in step (c). Preferred monomers are acrylic acid and/or acrylic amide.

Suitable monomers having a crosslinking group include, without the following being an exhaustive list, difunctionalized active esters, such as ethylene glycolbis[sulfosuccinimidyl-succinate] and bis[sulfosuccinimidyl]suberate, sulfosuccinimidyl[4-azidosalicylamido]-hexanoate, difunctional isocyanates, diacrylates such as 1,4-butanedioldiacrylate or α,ω-PEG-diacrylate and diepoxides such as ethyleneglycoldiglycidylether.

Alternatively, the crosslinking reaction can be switched such that the NCO, acrylate, epoxide, etc. functionality is on the grafted polymer, hence the crosslinking would be mediated by difunctional amines such as ethylenediamine and the like.

The grafting of the hydrophilic monomers on the polymer chains of the brush structure covalently attached to the tie layer according to step (c) yields a coating having for example a so-called bottle brush-type structure (BBT) composed of tethered "hairy" chains. Such BBT structures in one embodiment comprise a long hydrophilic backbone which carries relatively densely packed comparatively short hydrophilic side chains. Polymeric coatings of said BBT structures to a certain extent mimic highly water-retaining structures occurring in the human body, for example in cartilage or mucosal tissue.

The biomedical devices, e.g. ophthalmic devices obtained according to the invention have a variety of unexpected advantages over those of the prior art which make those devices very suitable for practical purposes, e.g. as contact lens for extended wear or intraocular lens. For example, they do have a high surface wettability, which can be demonstrated by their contact angles, their water retention and their water-film break up time or tear film break up time (TBUT).

The TBUT plays a particularly important role in the field of ophthalmic devices such as contact lenses. Thus the facile movement of an eyelid over a contact lens has proven important for the comfort of the wearer; this sliding motion is facilitated by the presence of a continuous layer of tear fluid on the contact lens, a layer, which lubricates the tissue/lens interface. However, clinical tests have shown that currently available contact lenses partially dry out between blinks, thus increasing friction between eyelid and the lens. The increased friction results in soreness of the eyes and reduced movement of the contact lenses. Now it has become feasible to considerably increase the TBUT of commercial contact lenses such as, for example, Lotrafilcon A lenses, by applying a surface coating according to the invention. On the base curve of a contact lens, the pronounced lubricity of the coating facilitates the on-eye lens movement, which is essential for extended wear of contact lenses. Moreover, the materials obtained by the process of the invention provide additional effects being essential for lenses for extended wear, such as an increased thickness of the pre-lens tear film which contributes substantially to low microbial adhesion and resistance to deposit formation. Due to the extremely soft and lubricious character of the novel surface coatings, biomedical articles such as in particular contact lenses coated by the process of the invention show a superior wearing comfort including improvements with respect to late day dryness and long term (overnight) wear. The novel surface coatings moreover interact in a reversible manner with ocular mucus, which contributes to the improved wearing comfort.

EXAMPLES

In the examples, if not indicated otherwise, amounts are amounts by weight, temperatures are given in degrees Celsius. Tear break-up time values in general relate to the pre-lens tear film non-invasive break-up time (PLTF-NIBUT) that is determined following the procedure published by M. Guillon et al., Ophthal. Physiol. Opt. 9, 355–359 (1989) or M. Guillon et al., Optometry and Vision Science 74, 273–279 (1997). Average advancing and receding water contact angles of coated and non-coated lenses are determined with the dynamic Wilhelmy method using a Krüss K-12 instrument (Krüss GmbH, Hamburg, Germany). Wetting force on the solid is measured as the solid is immersed in or withdrawn from a liquid of known surface tension. The molecular weight ("$M_w$") for the polymers utilized is set forth as an approximation.

Example A
(Layer-by-layer Functionalization for Creating Thick PAAm (Polyacrylamide) Tie Layers)

a) Iso-propanol-swollen Lotrafilcon A (polysiloxane/perfluoroalkylpolyether copolymer) contact lenses were dipped into a 0.13% PAA solution in water (MW of 90,000, pH of 2.5 by addition of HCl). The lenses were then thoroughly washed with acetonitrile, treated with isocyanatoethyl methacrylate (IEM) and then rinsed with water. The lenses were placed into a 5% acrylamide solution (1 g acrylamide in 20 ml of water). Solution and lenses were heated to 35° C. and nitrogen was purged for 10 minutes. Sodium persulphate was added (40 mg per 20 milliliters of solution). After 45 minutes, the lenses were washed in water overnight and the coating was evaluated.

b) A branched version of the PAAm-coated lens was then made by initially polymerizing with a 0.5% acrylic acid/4.5% acrylamide solution. The lenses were then retreated with IEM and then polymerized with acrylamide alone.

The resulting coated lenses were both highly lubricious and did not take up Sudan black staining and did not attract dust. These coatings proved to be abrasion resistant and, after finger rubbing rewashing, appeared to be uniformly wettable and cleaning. After autoclaving twice for 30 minutes each time, the lenses retained their properties.

Example B
(Swell Dipped PAA/PAH) Activated Lenses)

Iso-propanol-swollen Lotrafilcon A (polysiloxane/perfluoroalkylpolyether copolymer) contact lenses were dipped into an aqueous bicomponent solution of PAA/PAH (0.07% PAA with MW of 90,000 and 8.5 PPM of PAH having a MW of 50,000 to 65,000). The lenses were then water-rinsed and extracted with acetonitrile. IEM (2 pipette drops per lens) was used to attach the acrylate groups to the reactive polymeric layer. The lenses were placed into an aqueous 5% acrylamide solution and polymerized as described above in procedure b) of Example A.

A lubricious coating that was resistant to Sudan black staining was produced. These characteristics did not change after two 30-minute autoclaving cycles. These lenses withstood some finger rubbing abrasion.

In addition, a branched version was made by co-polymerizing acrylic acid with acrylamide (acrylic acid/acrylamide=1:9) and then washing and extracting with acetonitrile followed by reattaching IEM to the acrylic acid groups. After extraction of the lenses with water, a second polymerization with acrylamide was performed, resulting in a branched polyacrylamide structure.

Example C
(Swell Dipped PAA/PEI Activated Lenses)

Iso-propanol-swollen Lotrafilcon A (polysiloxane/perfluoroalkylpolyether copolymer) contact lenses were dipped into a 0.13% PAA solution (MW of 90,000, pH of 2.5 adjusted by HCl addition). After 5 minutes, the lenses were rinsed with water and then dipped into a 0.044% PEI solution (MW of 70,000, pH of 3.5 adjusted by HCl addition). The lenses were washed and extracted with acetonitrile, treated with isocyanatoethyl methacrylate (IEM) and then extracted with water. The lenses were placed into an aqueous 5% acrylamide solution and polymerized as described above in procedure a) of Example A. Nitrogen purging was performed and sodium persulphate was added at a rate of 40 milligrams per 20 milliliters of solution. The lenses were heated at 35° C. for 45 minutes. After this time, a viscous solution had formed and the lenses were removed by washing in excess water.

After overnight washing in water, the lenses were found to be lubricious to the touch and resistant to Sudan black staining. After autoclaving, the lenses continued to resist Sudan black staining and remained lubricous.

What is claimed is:

1. A process for coating a material surface, comprising the steps of:
   (a) applying to the material surface a tie layer comprising a polyionic material;
   (b) covalently binding a bifunctional compound comprising an ethylenically unsaturated double bond to the tie layer; and
   (c) graft polymerizing a hydrophilic monomer onto the compound comprising the ethylenically unsaturated double bond.

2. A process according to claim 1, wherein the material surface is the surface of an organic bulk material, in particular the surface of a biomedical device comprising an organic bulk material.

3. A process according to claim 1 or 2, wherein the tie layer of step (a) consists of one single polyionic material.

4. A process according to claim 1 or 2, wherein the tie layer of step (a) includes at least one bilayer comprising a polycationic material and a polyanionic material.

5. A process according to any one of claim 1, wherein the polyionic material of the tie layer comprises one or more polymers selected from the group consisting of a poly (allylamine hydrochloride), a poly(ethyleneimine), a poly (acrylic acid), and a poly(methacrylic acid).

6. A process according to any one of the claim 1, wherein the covalent bonding between the tie layer and the bifunctional compound comprising an ethylenically unsaturated double bond occurs via reaction of a hydroxy, amino, alkylamine, thiol or carboxy group, of the tie layer with an isocyanato, azlactone, epoxy, carboxy anhydride, carboxy or hydroxy group, of the ethylenically unsaturated compound.

7. A process according to any one of claim 1, wherein the ethylenically unsaturated compound is of formula:

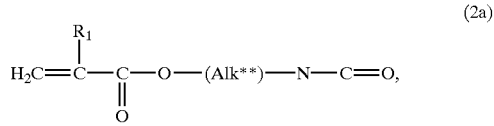
(2a)

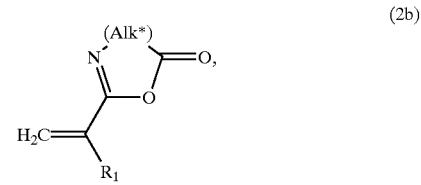
(2b)

-continued

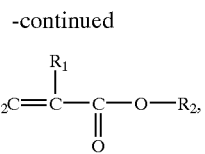
(2c)

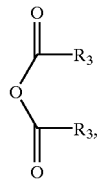
(2d)

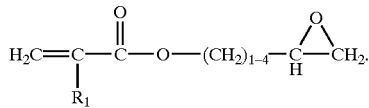
(2e)

wherein $R_1$ is hydrogen, $C_1$–$C_4$-alkyl or halogen;

$R_2$ is hydrogen, unsubstituted or hydroxy-substituted $C_1$–$C_6$-alkyl or phenyl;

$R_3$ and $R_3'$ are each an ethylenically unsaturated radical having from 2 to 6 C-atoms, or $R_3$ and $R_3'$ together form a bivalent radical —C($R_4$)═C($R_4'$)— wherein $R_4$ and $R_4'$ are each independently hydrogen, $C_1$–$C_4$-alkyl or halogen and (Alk*) is $C_1$–$C_6$-alkylene, and (Alk**) is $C_2$–$C_{12}$-alkylene.

8. A process according to claim 7, wherein, in step (b), the compound comprising an ethylenically unsaturated double bond is of formula (2a).

9. A process according to any one of the claim 1, wherein, in step c), the hydrophilic monomer is selected from the group consisting of acrylamide, acrylic acid, methacrylic acid, hydroxyethyl methacrylate, hydroxyethyl acrylate, methacrylamide, N,N-dimethylacrylamide, allylalcohol, N-vinylpyrrolidone and N,N-dimethylaminoethyl acrylate.

10. A process according to any one of claim 1, wherein in step (c), the monomer comprises one or more different monomers at least one of them comprising a reactive group.

11. A process according to any one of the claim 1, wherein in step (c), the monomer comprises a reactive group, (i) said reactive groups are reacted with a further compound comprising an ethylenically unsaturated double bond, (ii) a hydrophilic monomer and optionally a co-monomer having a crosslinkable group are graft-polymerized to said ethylenically unsaturated double bond, and (iii) in case crosslinkable groups being present in step (ii), crosslinking of said groups is initiated.

12. A process according to claim 11, wherein, in step (i), the further compound comprising an ethylenically unsaturated double bond is a compound of formula (2a)–(2e) according to claim 7.

13. A process according to claim 12, wherein, in step (ii) the hydrophilic monomer is selected from the group consisting of acrylic acid, acrylamide, N,N-dimethylacrylamide and N-vinylpyrrolidone and no co-monomer having a crosslinking group is present.

14. A coated material that is obtainable by the process of any one of the claim 1.

15. A coated material according to claim 14, which is a biomedical device.

16. A coated material according to claim 15, which is an ophthalmic device.

17. A coated material according to claim 16, which is a contact lens, intraocular lens or artificial cornea.

* * * * *